(12) United States Patent
Jeon et al.

(10) Patent No.: US 10,766,926 B2
(45) Date of Patent: Sep. 8, 2020

(54) COMPOSITION FOR AUTOPHAGY INHIBITING IN CELL, AND PHARMACEUTICAL COMPOSITION FOR PREVENTING OR TREATING TUMOR DISEASE, OR INHIBITING ANTI-CANCER AGENTS RESISTANCE CONTAINING THE SAME

(71) Applicant: L-BASE CO., LTD, Seoul (KR)

(72) Inventors: Do Yong Jeon, Seoul (KR); Chang Hoon Moon, Ulsan (KR); Ji Eun Jung, Gyeonggi-do (KR)

(73) Assignee: L-BASE CO., LTD, Seoul (KR)

( * ) Notice: Subject to any disclaimer, the term of this patent is extended or adjusted under 35 U.S.C. 154(b) by 0 days.

(21) Appl. No.: 15/780,347

(22) PCT Filed: May 28, 2018

(86) PCT No.: PCT/KR2018/006023
§ 371 (c)(1),
(2) Date: Dec. 5, 2018

(87) PCT Pub. No.: WO2019/208868
PCT Pub. Date: Oct. 31, 2019

(65) Prior Publication Data
US 2020/0087344 A1 Mar. 19, 2020

(30) Foreign Application Priority Data
Apr. 23, 2018 (KR) .................. 10-2018-0046935

(51) Int. Cl.
*A61K 38/00* (2006.01)
*C07K 7/06* (2006.01)
*A61P 35/00* (2006.01)

(52) U.S. Cl.
CPC ............... *C07K 7/06* (2013.01); *A61P 35/00* (2018.01); *A61K 38/00* (2013.01)

(58) Field of Classification Search
None
See application file for complete search history.

(56) References Cited

U.S. PATENT DOCUMENTS

| 6,652,861 B1 * | 11/2003 | Lee-Huang | C07K 14/415 424/185.1 |
| 2006/0292115 A1 * | 12/2006 | Drivas | A61K 38/2026 424/85.2 |
| 2013/0143251 A1 * | 6/2013 | Brik | C07K 1/026 435/24 |
| 2017/0027897 A1 | 2/2017 | Wang et al. | |

FOREIGN PATENT DOCUMENTS

| KR | 10-2015-0083195 A | 7/2015 | |
| KR | 10-2016-0105329 A | 9/2016 | |
| WO | WO-2004092207 A2 * | 10/2004 | ........... G01N 33/505 |

* cited by examiner

*Primary Examiner* — Jeanette M Lieb
(74) *Attorney, Agent, or Firm* — Vorys, Sater, Seymour & Pease LLP; Mih Suhn Koh

(57) ABSTRACT

Provided are a polypeptide having the activity of inhibiting autophagy in a cell, a composition for inhibiting autophagy in a cell, and particularly in a tumor cell, containing the polypeptide as an active ingredient, and a pharmaceutical composition containing the polypeptide, and more specifically, a composition for inhibiting autophagy in a cell containing a polypeptide inhibiting the control mechanism of autophagy as an active ingredient, and a pharmaceutical composition for preventing or treating a neoplastic disease or for inhibiting resistance to anticancer agents, containing the polypeptide.

15 Claims, 20 Drawing Sheets

Specification includes a Sequence Listing.

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: cancer-testis antigen protein

<400> SEQUENCE: 1

Ser Pro Thr Pro Lys Thr
1               5

<210> SEQ ID NO 2
<211> LENGTH: 7
<212> TYPE: PRT
<213> ORGANISM: Artificial Sequence
<220> FEATURE:
<223> OTHER INFORMATION: cancer-testis antigen protein

<400> SEQUENCE: 2

Gln Thr Ala Thr Ala Lys Ala
1               5

<210> SEQ ID NO 3
<211> LENGTH: 8
<212> TYPE: PRT
<213> ORGANISM: Artificial Sequence
<220> FEATURE:
<223> OTHER INFORMATION: cancer-testis antigen protein

<400> SEQUENCE: 3

Gly Asn Thr Ile Thr Ile Lys Thr
1               5
```

COMPOSITION FOR AUTOPHAGY INHIBITING IN CELL, AND PHARMACEUTICAL COMPOSITION FOR PREVENTING OR TREATING TUMOR DISEASE, OR INHIBITING ANTI-CANCER AGENTS RESISTANCE CONTAINING THE SAME

BACKGROUND OF THE INVENTION

Field of the Invention

The present invention relates to a polypeptide having the activity of inhibiting autophagy in a cell, a composition for inhibiting autophagy containing the polypeptide as an active ingredient, and a pharmaceutical composition containing the polypeptide, and more specifically, a composition for inhibiting autophagy in a cell, and particularly in a tumor cell, containing a polypeptide inhibiting the control mechanism of autophagy as an active ingredient, and a pharmaceutical composition for preventing or treating a neoplastic disease or inhibiting resistance to anticancer agents, containing the polypeptide.

Related Art

Autophagy is a process for removing unnecessary or impaired organelles and proteins from cells and it helps to maintain cell homeostasis and is a mechanism for cell survival.

Autophagy is known to play many roles especially in various diseases such as cancer, inflammatory diseases, degenerative neurological diseases, immunological diseases, etc. In particular, many studies have revealed that autophagy has complex roles according to the progression, type, genotype, etc. of cancer and is thus closely associated with cancer.

When cancer is formed by a rapid increase of cells, the cells become starved due to inappropriate supply of nutrients from the surrounding environment. At this time, the cells are provided with nutrients through autophagy by recycling harmful protein deposits and damaged organelles, and the energy supply by autophagy in an environment unfavorable for cancer growth promotes the survival of cancer cells.

The protein known to be involved in cell survival under these circumstances is AMP-activated protein kinase (AMPK). It is well known that AMP plays an important role in inducing metabolic action by being activated under the conditions of energy depletion, release of extracellular matrix, increase of reactive oxygen species, and hypoxia. Additionally, it is known that the activated AMPK inhibits the action of mammalian target of rapamycin (mTOR) in a signaling system of autophagy.

The mTOR is a serine/threonine protein kinase that belongs to PI3K-related kinase family and is known to regulate cell growth and proliferation, survival, migration, protein synthesis, and transcription, and inhibit autophagy. Many studies that have been published report that the mTOR mechanism is not only involved in cancer, but also in various diseases such as metabolic diseases, degenerative neurological diseases, cardiovascular diseases, etc.

Beclin1 is a protein encoded by the BECN1 gene and is an autophagy inducer. Beclin1 plays an important role in tumor suppression and this tumor suppressive function is known to be associated with programmed cell death of autophagy.

Recently, there is a growing interest in study results that autophagy plays an important role in the formation, growth, and treatment of tumors. The role of autophagy in cancer is so complex that it is known to have two opposite functions as a tumor suppressor or tumor promoter. Therefore, the differentiation and proper regulation of the role of autophagy in various conditions of cancer has become a new strategic method of cancer therapy, and study results have shown that the inhibition of autophagy reduces the resistance to anti-cancer agents, which is a major problem in cancer therapy, due to various chemotherapies (2017, Nature Reviews Cancer 17, 528-542).

Under these circumstances, the present inventors have made an effort to develop a polypeptide capable of controlling autophagy which plays an important role in cancer. As a result, they have confirmed that a composition for inhibiting autophagy in a cell, and particularly in a tumor cell, containing a polypeptide inhibiting the control mechanism of autophagy as an active ingredient, and a pharmaceutical composition for preventing or treating a neoplastic disease or inhibiting resistance to anticancer agents, containing the polypeptide, have the effects of inhibiting the promotion of tumor growth caused by autophagy and reducing resistance to anticancer agents, by activating mTOR that inhibits autophagy and inhibiting autophagy through the inactivation of AMPK and Beclin1 that induce autophagy, thereby completing the present invention.

PRIOR ART REFERENCES (Patent Document 1) KR10-1645359 B
(Patent Document 2) KR10-2018-0007307 A

SUMMARY OF THE INVENTION

An object of the present invention is to provide a polypeptide, which has an activity of inhibiting the promotion of tumor growth caused by autophagy and reducing resistance to anticancer agents in a cell, and particularly in a tumor cell, by activating mTOR that inhibits autophagy and inhibiting autophagy through the inactivation of AMPK and Beclin1 that induce autophagy.

Another object of the present invention is to provide a composition for inhibiting autophagy in a cell, and particularly in a tumor cell, using the polypeptide.

Still another object of the present invention is to provide a pharmaceutical composition for preventing or treating a neoplastic disease using the polypeptide.

Still another object of the present invention is to provide a pharmaceutical composition for inhibiting resistance to anticancer agents using the composition for inhibiting autophagy.

According to an aspect of the present invention, it provides a polypeptide having the activity of inhibiting autophagy in a cell, represented by General Formula of a sequence below:

$$X3\text{-}X1\text{-}T\text{-}X1\text{-}K\text{—}X2 \qquad \text{[General Formula]}$$

in which, in General Formula of a sequence above,
T is threonine,
K is lysine;
X1 is at least one amino acid selected from the group consisting of alanine, glycine, isoleucine, leucine, methionine, proline, and valine;
X2 is at least one amino acid selected from the group consisting of alanine, threonine, cysteine, asparagine, proline, glutamine, and serine; and X3 is at least one amino acid selected from the group consisting of alanine, glutamine, threonine, serine, asparagine, and glycine, or is absent.

Autophagy is induced in a cell that is under stress by a cell survival mechanism. Although autophagy inhibits tumor before the onset of cancer or during the development of cancer, it contributes to the survival of tumor cells once cancer is developed. Therefore, it is thought that autophagy can reduce the activity of tumor cells by inhibiting the mechanism of autophagy in tumor cells where cancer has developed.

In this regard, the present inventors have invented a polypeptide for inhibiting autophagy in cells where cancer has developed, and particularly in tumor cells, and have confirmed that the polypeptide represented by General Formula can inhibit the promotion of tumor growth caused by autophagy and reducing resistance to anticancer agents, by inhibiting autophagy, thereby completing the present invention.

In the polypeptide having the activity of inhibiting autophagy of the present invention, the cell may be a tumor cell.

As used herein, the term "in a tumor cell" may refer to a tumor cell after cancer development, and may refer to solid cancer. Additionally, the term "tumor cell" may refer to a tumor cell having resistance to anticancer agents.

In the polypeptide having the activity of inhibiting autophagy of the present invention, X1 may be an amino acid which is non-polar and has an aliphatic R group, and preferably X1 may be alanine, and X2 may be an amino acid which is non-polar and has an uncharged R group, and preferably X2 may be alanine.

Additionally, in the polypeptide having the activity of inhibiting autophagy of the present invention, X1 may be an amino acid which is non-polar and has an aliphatic R group, and preferably proline, and X2 may be an amino acid which is polar and has an uncharged R group, and preferably threonine.

Additionally, in the polypeptide having the activity of inhibiting autophagy of the present invention, X1 may be an amino acid which is non-polar and has an aliphatic R group, and preferably isoleucine, and X2 may be an amino acid which is polar and has an uncharged R group, and preferably threonine.

In the polypeptide having the activity of inhibiting autophagy of the present invention, X3 may be glutamine or threonine.

Additionally, in the polypeptide having the activity of inhibiting autophagy of the present invention, X3 may be serine.

In the polypeptide having the activity of inhibiting autophagy of the present invention, X3 may be glycine, asparagine, or threonine.

The polypeptide having the activity of inhibiting autophagy of the present invention inhibits autophagy in a cell by reducing the expression of at least one protein selected from the group consisting of p-AMPK, ATG5-ATG12, Beclin1, p-Beclin1, LC3-I, and LC3-II.

According to an embodiment, as a result of confirming the association of proteins involved in the autophagy mechanism between non-small cell lung cancer cell lines, it was confirmed that the expression of p-AMPK, ATG5, and ATG5-ATG12 increased in non-small cell lung cancer cell lines resistant to anticancer agents and the expression of p62 protein was decreased, compared to non-small cell lung cancer cell lines.

p-AMPK is a factor that increases tumor growth and resistance to anticancer agents caused by autophagy, ATG5 is a tumor-promoting factor, and ATG5-ATG12 is an essential factor in charge of the formation of autophagosomes in autophagy, and thus the increase in the expression of p-AMPK, ATG5, and ATG5-ATG12 means that the polypeptide according to the present invention is involved in resistance of cancer cells (see Example 1 and FIGS. 1 to 3A and 3B). That is, according to an embodiment of the present invention, the increase in the expression of p-AMPK, ATG5, and ATG5-ATG12 means the involvement of resistance of cancer cells (see Example 1 and FIGS. 1 to 3A and 3B).

As a result of treatment of the polypeptide of the present invention according to concentrations on the non-small cell lung cancer cell line resistant to anticancer agents, it was confirmed that the expression of Beclin1, p-Beclin1, ATG5-ATG12, LC3-I, and LC3-II proteins, which are known as initiators of autophagy, was decreased. These results suggest that the polypeptide according to the present invention can inhibit promotion of tumor growth and reduce resistance to anticancer agents by inhibiting autophagy via reduction of expression of the proteins which are known as activators of the autophagy (see Example 2 and FIGS. 4 to 6).

In the polypeptide having the activity of inhibiting autophagy of the present invention, the inhibition of autophagy in a tumor cell may inhibit autophagy in a cell by increasing the expression of p-mTOR or p62 protein.

According to an embodiment of the present invention, as a result of confirming the effect of inhibiting autophagy, antitumor effect, and effect of inhibiting resistance anticancer agents of the polypeptide of the present invention, it was confirmed that when the polypeptide of the present invention was introduced into mice according to concentrations, the concentration of tumor tissue decreased in a concentration-dependent manner (see Example 4 and FIGS. 8A, 8B and 8C).

Additionally, as a result of confirming the expression levels of the factors involved in autophagy in the tumor tissue, it was confirmed that expression of p-mTOR and p62 proteins, which play the role of inhibiting autophagy, was increased, whereas the expression of p-AMPK, Beclin1, and p-Beclin1 proteins, which are activators of autophagy, were decreased.

These results suggest that the polypeptide of the present invention can reduce the promotion of tumor growth and reduce resistance to anticancer agents by inactivating p-AMPK, Beclin1, and p-Beclin1 which induce autophagy, by increasing the factors that inhibit autophagy (see Example 4 and FIG. 9).

In the polypeptide having the activity of inhibiting autophagy of the present invention, the polypeptide may be labeled with any one labeling material selected from the group consisting of chromogenic enzymes, radioisotopes, chromophores, luminescent materials, fluorescers, magnetic resonance imaging (MRI) materials, super paramagnetic particles, and ultrasuper paramagnetic particles, however, it does not necessarily mean that the polypeptide can be labeled with a labeling material.

According to another aspect of the present invention, the present invention provides a composition for inhibiting autophagy in a cell containing the polypeptide represented by General Formula below as an active ingredient:

X3-X1-T-X1-K—X2    [General Formula]

in which, in General Formula of a sequence above,

T is threonine,

K is lysine;

X1 is at least one amino acid selected from the group consisting of alanine, glycine, isoleucine, leucine, methionine, proline, and valine;

X2 is at least one amino acid selected from the group consisting of alanine, threonine, cysteine, asparagine, proline, glutamine, and serine; and X3 is at least one amino acid selected from the group consisting of alanine, glutamine, threonine, serine, asparagine, and glycine, or is absent.

According to still another aspect of the present invention, the present invention provides a pharmaceutical composition for preventing or treating a neoplastic disease containing the polypeptide represented by General Formula below as an active ingredient:

X3-X1-T-X1-K—X2      [General Formula]

in which, in General Formula of a sequence above,

T is threonine,

K is lysine;

X1 is at least one amino acid selected from the group consisting of alanine, glycine, isoleucine, leucine, methionine, proline, and valine;

X2 is at least one amino acid selected from the group consisting of alanine, threonine, cysteine, asparagine, proline, glutamine, and serine; and X3 is at least one amino acid selected from the group consisting of alanine, glutamine, threonine, serine, asparagine, and glycine, or is absent.

In the pharmaceutical composition for preventing or treating a neoplastic disease of the present invention, the neoplastic disease may be one selected from the group consisting of lung cancer, liver cancer, colon cancer, pancreatic cancer, stomach cancer, breast cancer, ovarian cancer, kidney cancer, thyroid cancer, parathyroid cancer, esophageal cancer, prostate cancer, brain cancer, skin cancer, osteosarcoma, soft tissue sarcoma, glioma, lymphoma, nasopharyngeal cancer, larynx cancer, adrenal gland cancer, colon carcinoma, ureteral cancer, gallbladder cancer, bladder cancer, testis cancer, uterine cervical cancer, endometrial cancer, choriocarcinoma, head and neck cancer, malignant melanoma, leukemia, multiple myeloma, chronic myeloid leukemia, neuroblastoma, and aplastic anemia, and preferably lung cancer or breast cancer, but the neoplastic disease is not limited thereto.

In the pharmaceutical composition for preventing or treating a neoplastic disease of the present invention, the composition may be used as a pharmaceutical composition for diseases that can be prevented or treated by inhibiting autophagy, and preferably as a pharmaceutical composition for preventing or treating a neoplastic disease.

According to still another aspect of the present invention, the present invention provides a pharmaceutical composition for inhibiting resistance to anticancer agents containing the polypeptide represented by General Formula below as an active ingredient:

X3-X1-T-X1-K—X2      [General Formula]

in which, in General Formula of a sequence above,

T is threonine,

K is lysine;

X1 is at least one amino acid selected from the group consisting of alanine, glycine, isoleucine, leucine, methionine, proline, and valine;

X2 is at least one amino acid selected from the group consisting of alanine, threonine, cysteine, asparagine, proline, glutamine, and serine; and X3 is at least one amino acid selected from the group consisting of alanine, glutamine, threonine, serine, asparagine, and glycine, or is absent.

In the pharmaceutical composition for inhibiting resistance to anticancer agents of the present invention, the composition may have resistance to any anticancer agent used to treat a neoplastic disease, and preferably have resistance to at least one anticancer agent selected from the group consisting of erlotinib, celastrol, cisplatin, docetaxel, osimertinib, taxol, pemetrexed, and tamoxifen.

In the pharmaceutical composition for inhibiting resistance to anticancer agents of the present invention, the composition may inhibit resistance to anticancer agents by inhibiting autophagy.

According to an embodiment, as a result of treating PC9-ER, H1975, and MCF7R (i.e., cancer cell lines having resistance to various anticancer agents) with the polypeptide of the present invention, it was confirmed that cell growth was inhibited (see FIGS. 6, 11A, 11B, 14A, 14B and 14C).

These results suggest that the polypeptide of the present invention can inhibit (reduce) resistance to anticancer agents in cancer cell lines, which have resistance to anticancer agents, by inhibiting autophagy.

The pharmaceutical composition according to the present invention may be provided in a pure form of the polypeptide or by formulating it into a suitable form together with a pharmaceutically acceptable carrier. As used herein, the term "pharmaceutically acceptable" refers to a non-toxic composition that does not normally cause allergic reactions such as gastrointestinal disorders, dizziness, etc. when it is physiologically acceptable and administered to humans. Examples of the carrier may include all kinds of solvents, dispersion media, oil-in-water or water-in-oil emulsions, aqueous compositions, liposomes, microbeads and microsomes, biodegradable nanoparticles, etc., but the pharmaceutically acceptable carrier is not limited thereto.

Meanwhile, the pharmaceutical composition according to the present invention may be formulated together with a pharmaceutically acceptable carrier according to administration routes. The administration routes according to the present invention may include oral or parenteral administration, but the administration routes are not limited thereto. Examples of the parenteral administration routes may include various routes such as transdermal, nasal, peritoneal, muscular, subcutaneous, or intravenous, but the parenteral administration routes are not limited thereto.

In a case where the pharmaceutical composition according to the present invention is orally administered, the pharmaceutical composition of the present invention may be formulated in the form of powders, granules, tablets, pills, sugar-coated tablets, capsules, solutions, gels, syrups, suspensions, wafers, etc. together with a pharmaceutically acceptable carrier for oral administration according to methods known in the art, but the formulation type is not limited thereto.

The pharmaceutical composition of the present invention may be formulated according to methods known in the art so as to provide rapid, sustained, or delayed release of an active ingredient after administration to mammals.

The pharmaceutical composition formulated by the above methods may be administered in an effective amount via various routes including oral, transdermal, subcutaneous, intravenous, or muscular administration. As used herein, the term "effective amount" refers to an amount of substance that enables the tracking of diagnosis or therapeutic effect when administered to a patient.

The dosage of the pharmaceutical composition according to the present invention may be appropriately selected according to the administration route, subject to be treated, disease to be treated and its severity, age, sex, body weight, individual difference, and disease state. Preferably, the pharmaceutical composition containing the polypeptide of the present invention may vary depending on the severity of the disease, and conventionally, the active ingredient content may be repeatedly administered several times a day with an effective dose of 1 mg to 1,000 mg per single administration based on adults.

BRIEF DESCRIPTION OF THE DRAWINGS

FIGS. 1 to 3A and 3B show the results according to Example 1 of the present invention.

DESCRIPTION OF EXEMPLARY EMBODIMENTS

Hereinafter, the present invention will be described in more detail with reference to Examples. Since these Examples are for illustrating the present invention only, the scope of the present invention is not construed as being limited by these Examples.

Example 1: Confirmation of Autophagy Mechanism in Cancer Cell Lines

The cancer cell line (PC9) used in the present invention was cultured in a minimum essential medium in a conditioned incubator (37° C.) supplemented with 10% fetal bovine serum and antibiotics. The cancer cell line (PC9-ER) was constructed to have resistance by exposing to erlotinib as an anticancer agent for a long period of time.

Figure 1:
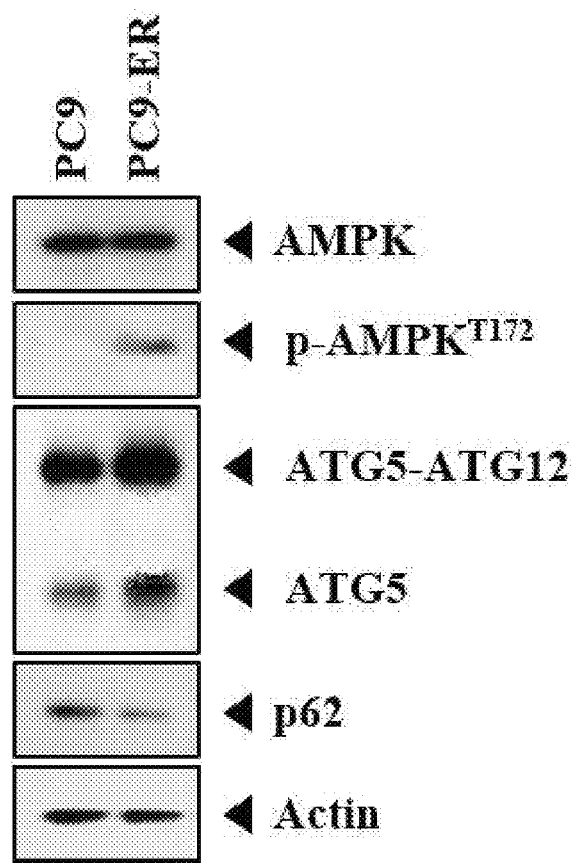

In order to examine whether proteins with a mechanism controlling autophagy are involved in the cancer cell line (PC9) and the cell line (PC9-ER), which has resistance to anticancer agents, the expression levels of AMP-activated protein kinase (AMPK), phosphorylated AMPK (p-AMPK), autophagy-related genes 5 (ATG5), ATG5-ATG12, and p62 proteins were compared by western blot method, and the results are shown in FIG. 1.

As a result, as can be seen in FIG. 1, it was confirmed that the cell line (PC9-ER), which has resistance to anticancer agents, showed an increase of the expression levels of p-AMPK, ATG5, and ATG5-ATG12 compared to those of the PC9 cell line, and it was also confirmed that the expression level of p62 protein, which is an autophagy-inhibiting molecule, was lowered.

Additionally, the PC9 cell line and the PC9-ER cell line were subjected to immunofluorescence staining.

Specifically, the PC9 cell line and the PC9-ER cell line were fixed at room temperature using 4% formaldehyde. Then, the cells were reacted at room temperature for 30 minutes so as to prevent inaccurate binding to antibodies using PBS containing 0.1% BSA, and allowed to react with LC3 antibodies (cell signaling) at 4° C. for 24 hours. After removing the antibodies, the cells were washed with PBS and allowed to react with secondary antibodies (Thermo Fisher) labeled with Alexa 488 fluorescence at room temperature for 1.5 hours. After the reaction, the cells from which antibodies were removed were washed with PBS and stained with DAPI (Thermo Fisher) for 1 minute. The fluorescent staining was confirmed by confocal microscopy and the results are shown in FIG. 2.

Figure 2:
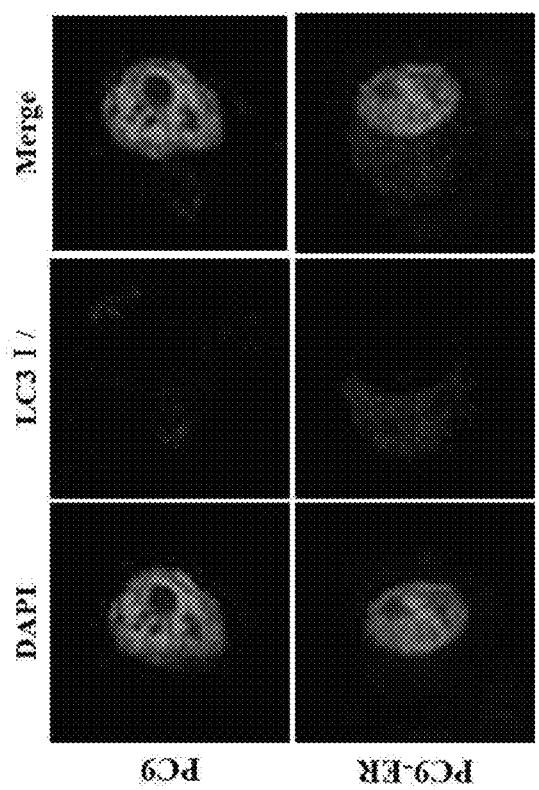

As a result, as can be seen in FIG. 2, it was confirmed that the expression level of LC3 puncta was higher in the PC9-ER cell line compared to that in the PC9 cell line.

Additionally, the MTT assay was performed so as to confirm the resistance of the PC9 cell line and the PC9-ER cell line to anticancer agents.

Specifically, an equal number of the PC9 cell line and the PC9-ER cell line were cultured in a 96-well cell culture plate, treated with an anticancer agent subjected to a $\frac{1}{10}$-fold serial dilution for 24 hours, and confirmed using MTT. As an experiment to utilize the principle that NADH present in the mitochondria of a living cell reacts with MTT to form formazan, formazan was dissolved in DMSO and its absorbance was measured at 570 nm and thereby the growth activity of the cells was confirmed. The results are shown in FIGS. 3A and 3B.

Figure 3A:
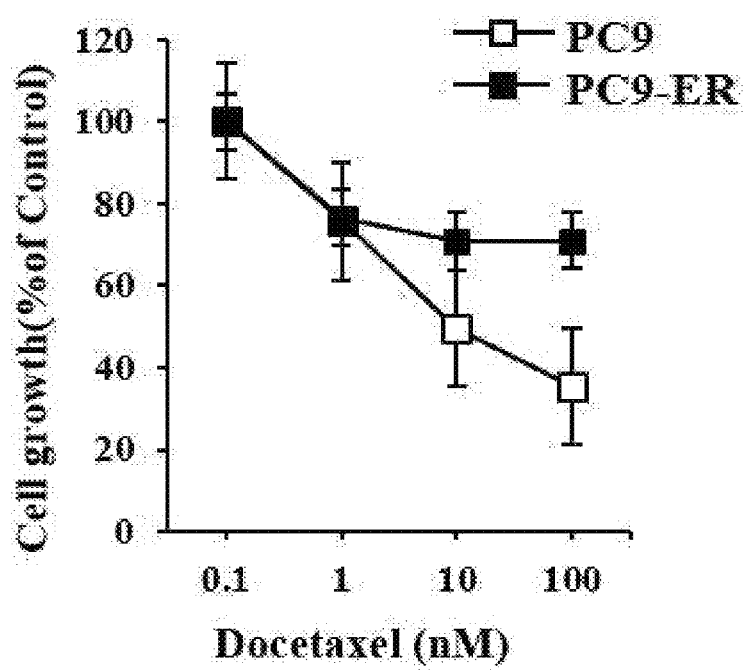
Figure 3B:
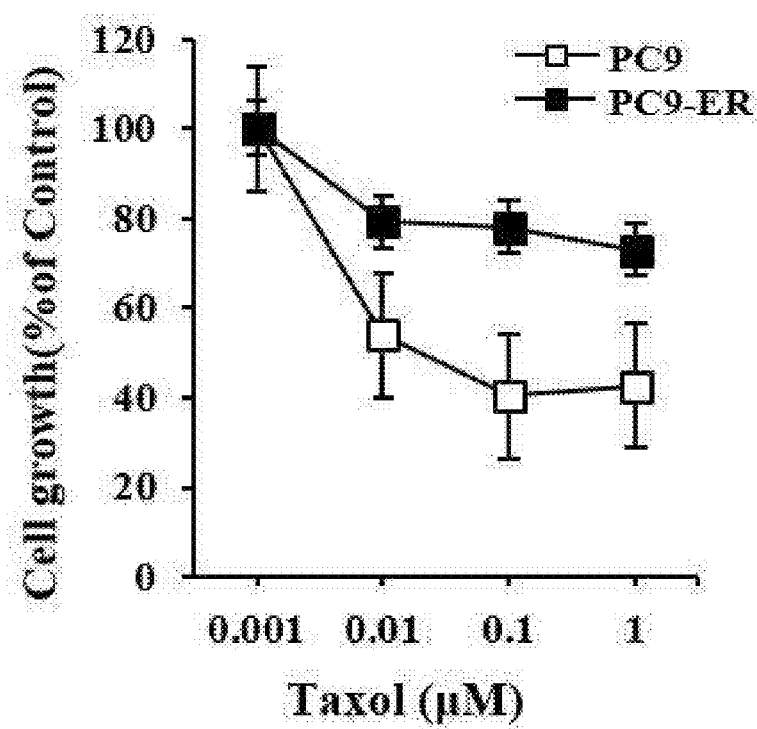

As a result, as can be seen in FIGS. 3A and 3B, it was confirmed that the PC9-ER cell line, in which the mechanism controlling autophagy was further activated, had higher resistance to docetaxel and taxol (i.e., known anticancer agents) compared to that of PC9 cell line.

Example 2: Confirmation of Effect of Polypeptide in Autophagy Control

An attempt was made to confirm the inhibitory effects of SPTPKT (polypeptide 1) and QTATAKA (polypeptide 2) against autophagy, based on the results that the expression of ATG5 and ATG5-ATG12 proteins which are known to be involved in autophagy in the cancer cell line (PC9-ER).

Figure 4:
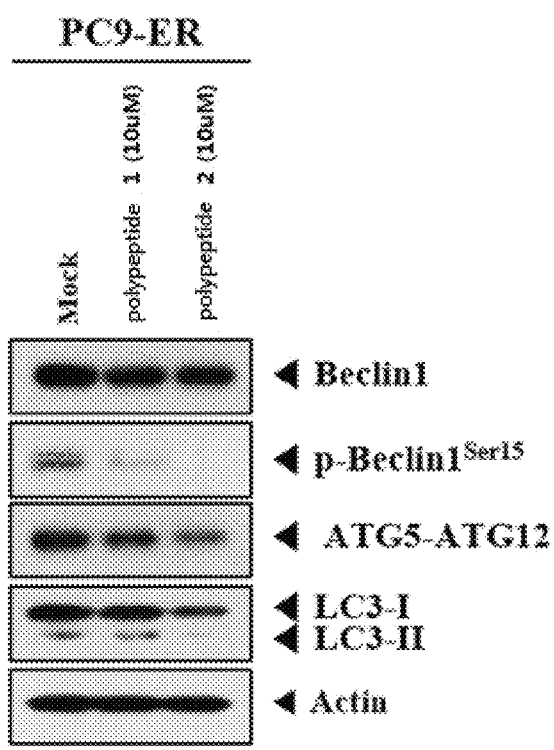
FIGS. 4 to 6 show the results according to Example 2 of the present invention.

Specifically, the PC9-ER cell line was treated with each of the polypeptide 1 and the polypeptide 2 and the expression levels of Beclin1, p-Belclin1, ATG5-ATG12, LC3 I, and LC3 II (i.e., proteins associated with autophagy mechanism) were compared by western blot method, and the results are shown in FIG. 4.

As a result, as can be seen in FIG. 4, it was confirmed that the expression levels of Beclin1 and p-Beclin1, which are known as autophagy initiators, and ATG5-ATG12, LC3 I, and LC3 II proteins, which are autophagy-activating molecules, were lowered when the PC9-ER cell line was treated with the polypeptide 1 and the polypeptide 2, respectively.

Additionally, the cells were subjected to immunofluorescence staining after treating the PC9-ER cell line with the polypeptide 2.

Specifically, 24 hours after treating the PC9-ER cell line with the polypeptide 2, the cells were fixed at room temperature using 4% formaldehyde. Then, the cells were reacted at room temperature for 30 minutes so as to prevent inaccurate binding to antibodies using PBS containing 0.1% BSA, and allowed to react with LC3 antibodies (cell signaling) at 4° C. for 24 hours. After removing the antibodies, the cells were washed with PBS and allowed to react with secondary antibodies (Thermo Fisher) labeled with Alexa 488 fluorescence at room temperature for 1.5 hours. After the reaction, the cells from which antibodies were removed were washed with PBS and stained with DAPI (Thermo Fisher) for 1 minute. The fluorescent staining was confirmed by confocal microscopy and the results are shown in FIG. 5.

Figure 5:
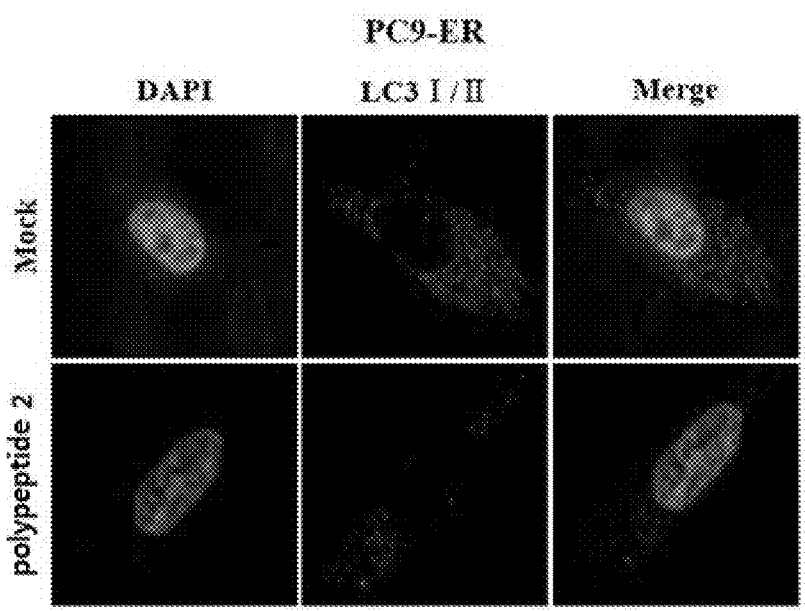

As a result, as can be seen in FIG. 5, it was confirmed that the expression level of LC3 puncta was lowered in the PC9-ER cell line.

Additionally, the PC9-ER cell line was treated with the polypeptide 1, polypeptide 2, and GNTITIKT (polypeptide 3), respectively, and the MTT assay was performed so as to confirm the resistance of the PC9-ER cell line to anticancer agents.

Specifically, the PC9-ER cell line was plated on a 96-well cell culture plate and treated with each of the polypeptides (1 to 3) for 24 hours. Then, the cells were treated for with an anticancer agent subjected to a 1/10-fold serial dilution for 24 hours and confirmed using MTT. As an experiment to utilize the principle that NADH present in the mitochondria of a living cell reacts with MTT to form formazan, formazan was dissolved in DMSO and its absorbance was measured at 570 nm and thereby the growth activity of the cells was confirmed. The results are shown in FIG. 6.

Figure 6:
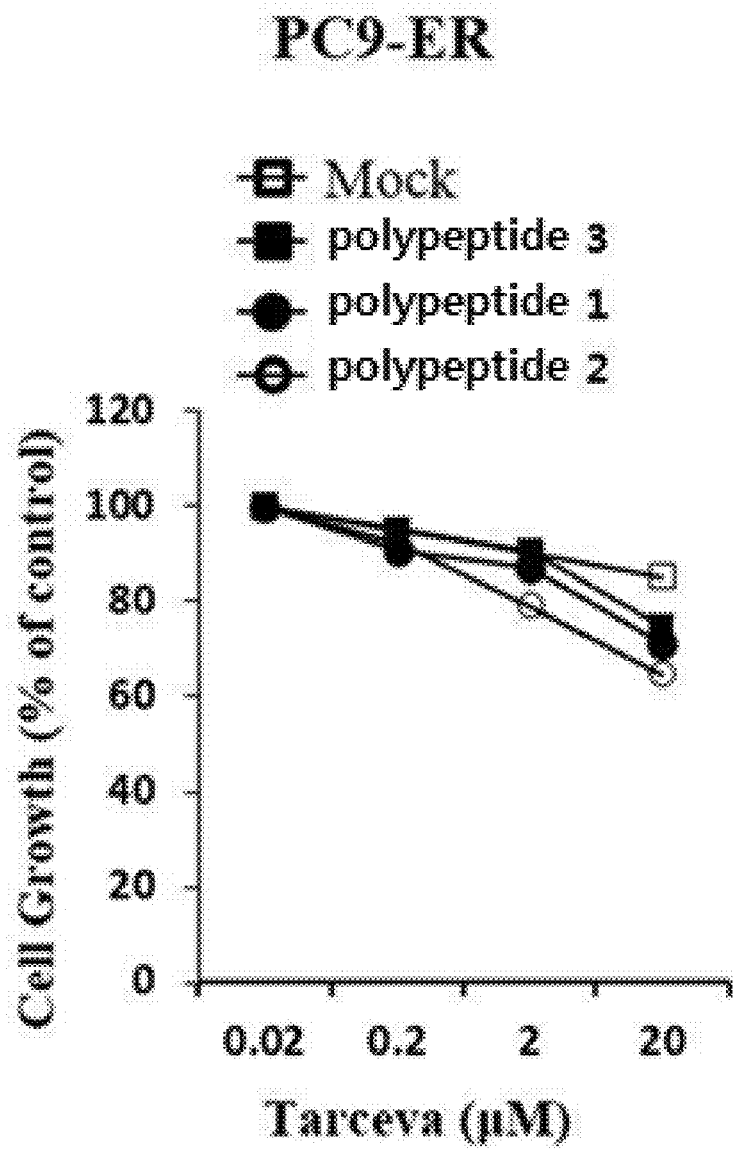

As a result, as can be seen in FIG. 6, it was confirmed that each of the polypeptides (1 to 3) treatment reduced resistance to erlotinib (Tarceva), which is an anticancer agent, in the PC9-ER cell line.

These results suggest that the polypeptide 1, polypeptide 2, and polypeptide 3 have an inhibitory effect against autophagy in the cancer cell line having resistance to anticancer agents.

Example 3: Confirmation of Intracellular Expression of Polypeptides

As in the method of immunofluorescence staining method according to Example 1 of the present invention, the polypeptide 2 was labeled with green fluorescence (fluorescein isothiocyanate; FITC) and transfected into the PC9-ER cell line according to a known method. The results are shown in FIG. 7.

Figure 7:
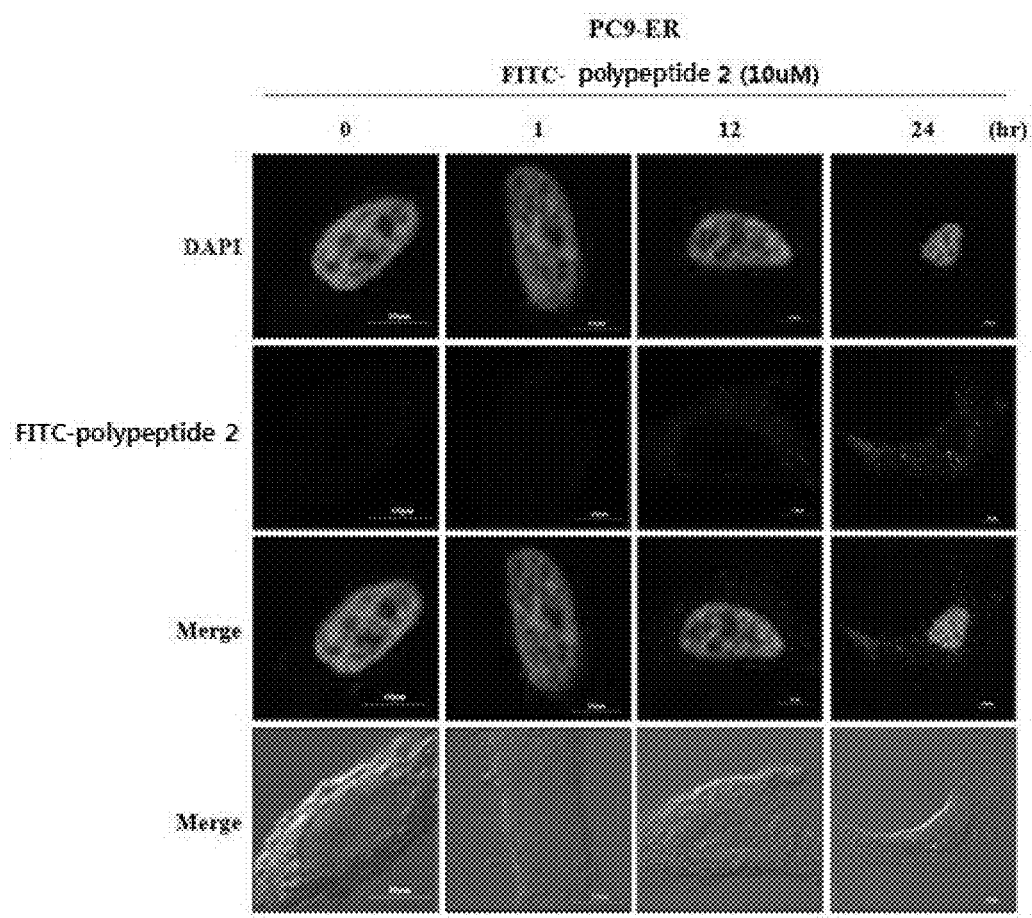
FIG. 7 shows the results according to Example 3 of the present invention.

As a result, as can be seen in FIG. 7, it was confirmed that FITC-polypeptide 2 is delivered into the cells in a time-dependent manner.

Example 4: Confirmation of Inhibitory Effect of Polypeptides Against Tumor Formation An attempt was made to confirm the in-vivo anticancer action of the polypeptide 2 based on the results that the polypeptide 2 showed an anticancer action through autophagy in in-vivo condition.

Specifically, athymic nude mice (BALB/C nude, 5 to 6-week old females) were subcutaneously injected on the side with the PC9-ER cell line ($2 \times 10^6$ cells/mouse) to induce tumor. When the tumor volume reached about 150 mm³, the polypeptide 2 was injected a total of 5 times through the caudal vein and the changes in the tumor size were examined. The tumor volume was directly measured using a caliper and calculated by the following equation (length×width×height×0.5). In order to confirm the inhibitory effect of the polypeptide 2 against tumor formation, the peptide (at concentrations of 0 μg/mouse, 50 μg/mouse, 100 μg/mouse, and 200 μg/mouse) was injected 5 times through the caudal vein from day 25 at 3 day intervals. On the 41$^{st}$ day, the tumors were separated and the sizes of the tumor volumes were measured, and western blot was performed using each labeled antibody. The results are shown in FIGS. 8A, 8B, 8C, and 9.

Figure 8A:
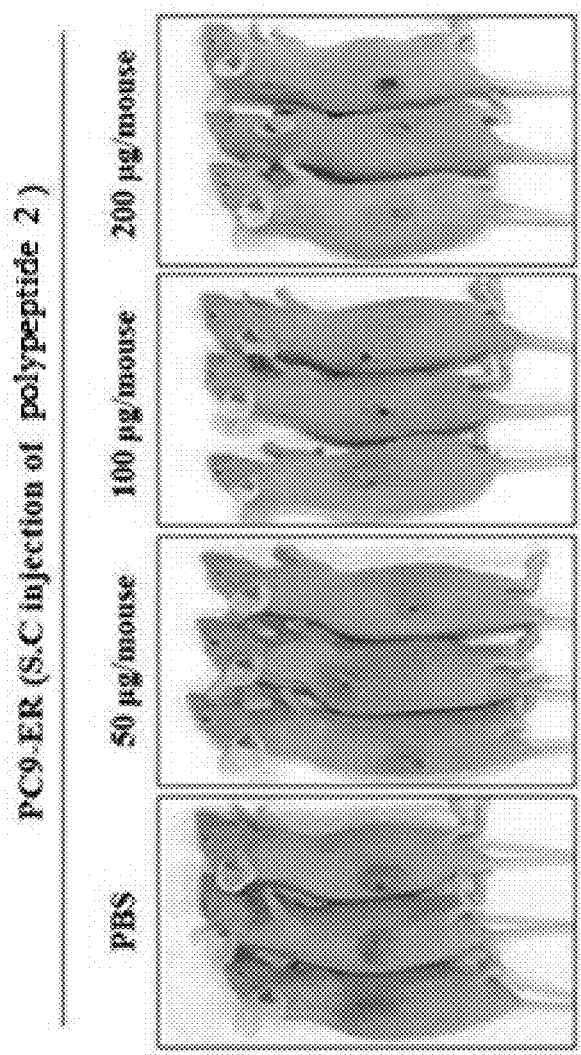
FIGS. 8A, 8B, 8C, and 9 show the results according to Example 4 of the present invention.
Figure 8B:
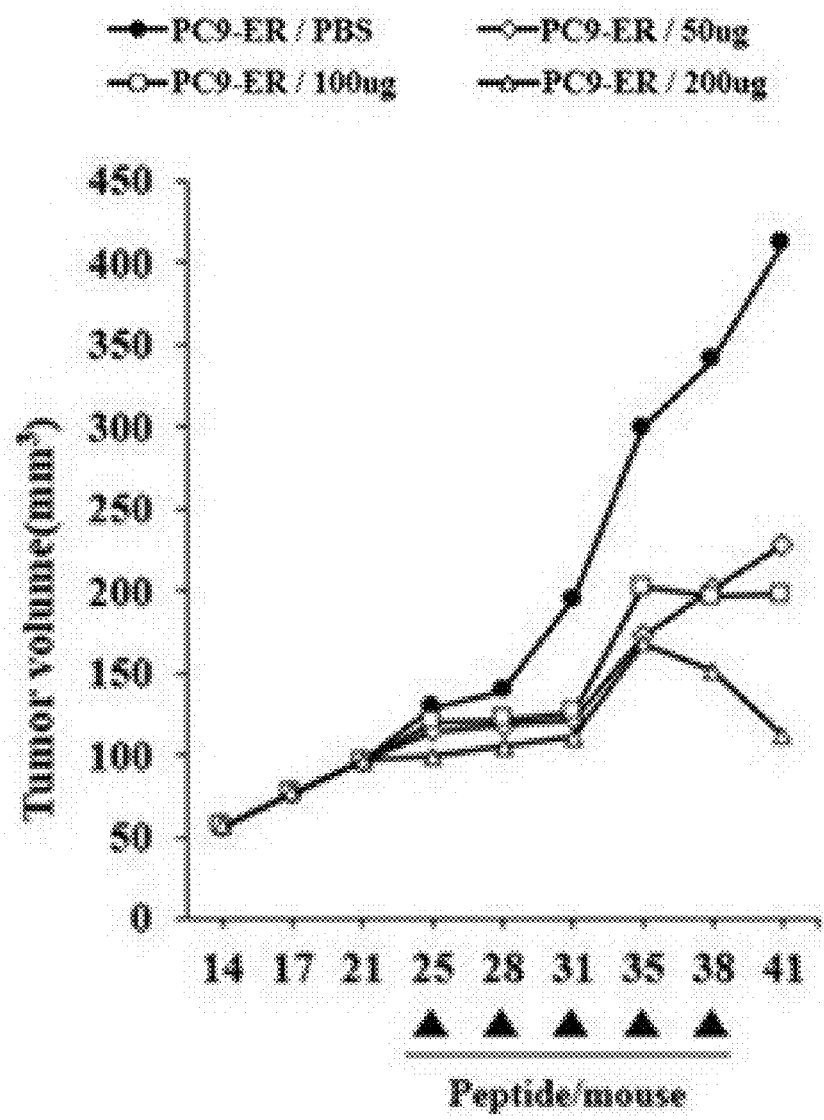
Figure 8C:
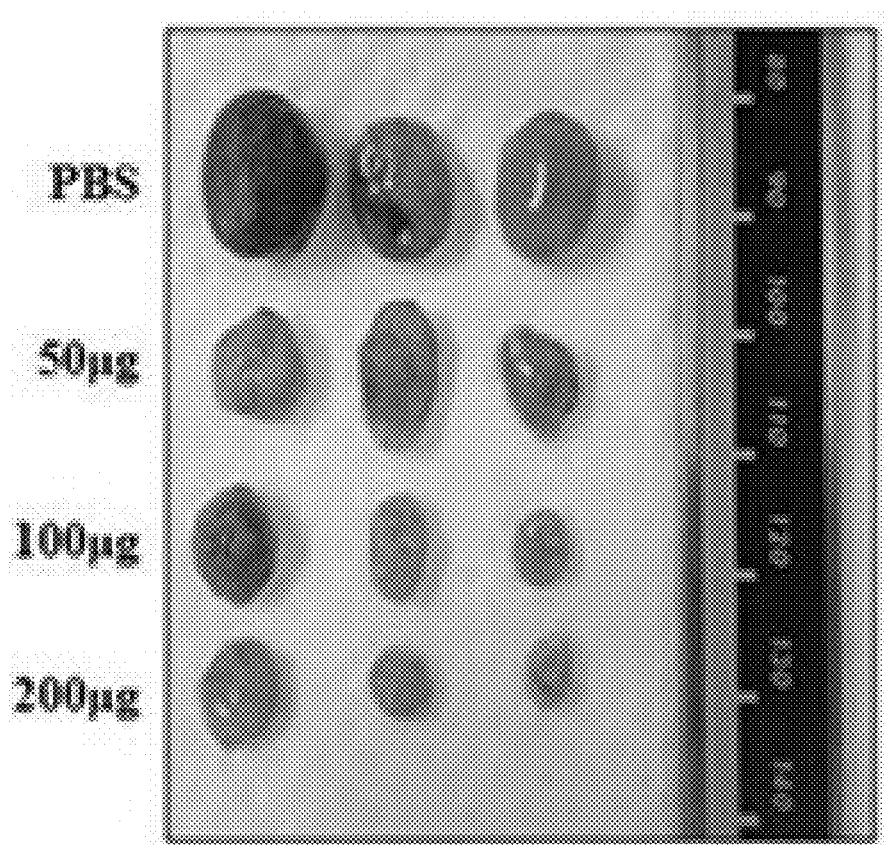

As a result, as can be seen in FIG. 8A, 8B, 8C, it was confirmed that the polypeptide 2 significantly reduced the size of tumors.

Figure 9:
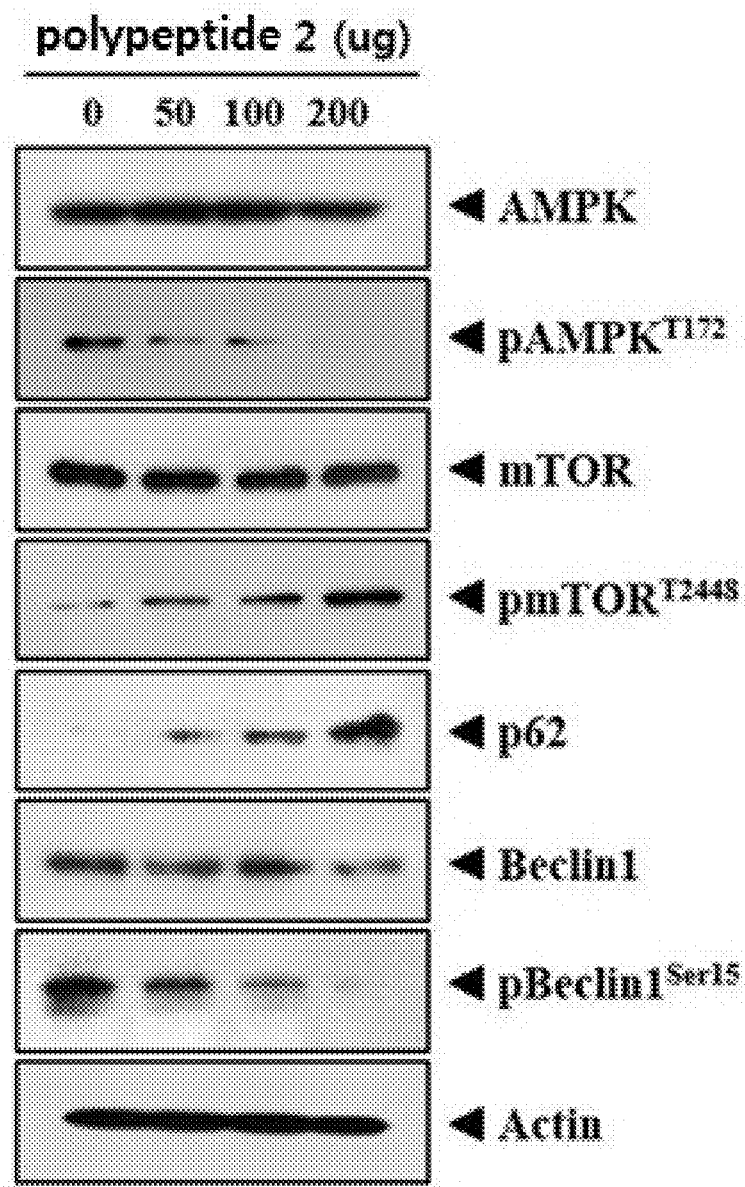

Additionally, as can be seen in FIG. 9, the tumor tissue showed a phenomenon that the expression of p-mTOR and p62 proteins increased in a concentration-dependent manner, and the expression of p-AMPK, Beclin1, and p-Beclin1 proteins decreased in a concentration-dependent manner.

These results show the anticancer action of the polypeptide 2 by the inhibition of the autophagy mechanism.

Example 5: Confirmation of Effect of Polypeptides on Controlling Autophagy

To examine the effect of anticancer activity of the polypeptide 1 and the polypeptide 2 through autophagy controlling proteins in H1975, which is a different non-small cell lung cancer cell line from those in Examples 1 to 4, western blot was performed using each of the labeled antibody in H1975 cells. The results are shown in FIG. 10.

Figure 10:
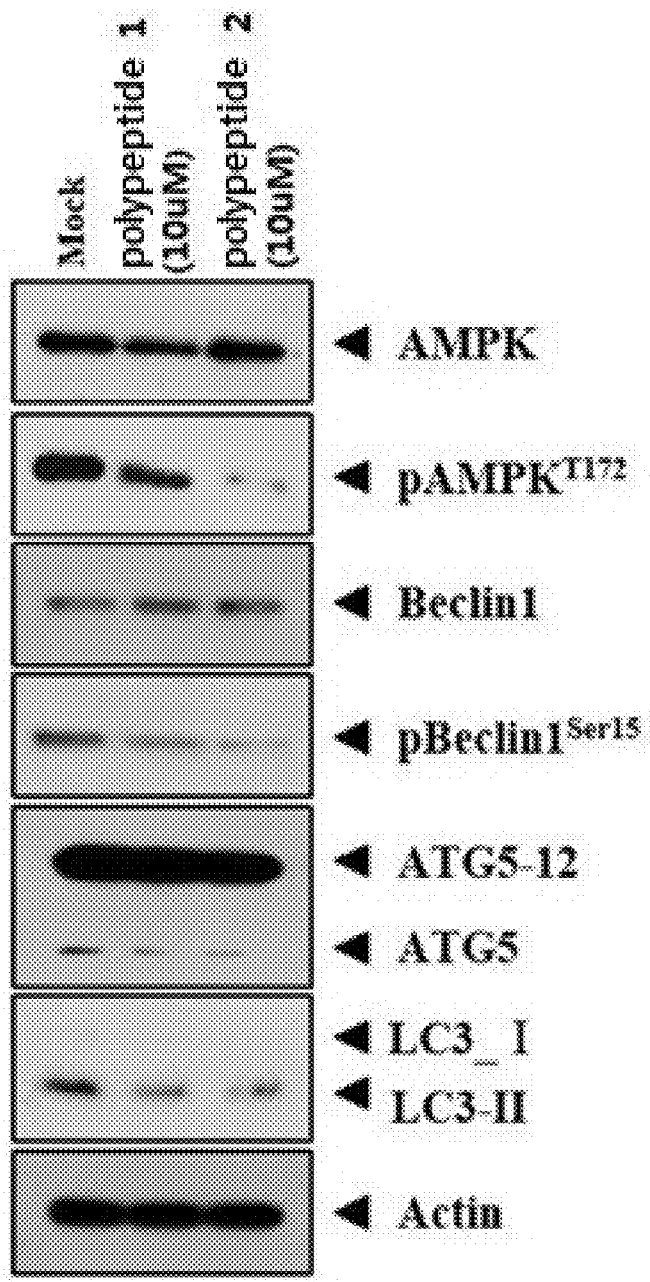
FIGS. 10, 11A, and 11B show the results according to Example 5 of the present invention.

As a result, as can be seen in FIG. 10, it was confirmed that when treated with the polypeptide 1 and the polypeptide 2, respectively, the expression of p-AMPK, which is known to be involved in cancer controlling mechanism, and those of p-Beclin1, ATG5, ATG5-ATG12, LC3 I, and LC3 II, which are proteins involved in autophagy controlling mechanism, were lowered.

Additionally, after the treatment with the polypeptide 1, polypeptide 2, and polypeptide 3, respectively, the MTT assay was performed so as to confirm the resistance to osimertinib (Tagrisso), an anticancer agent.

Specifically, an equal number of cells of the H1975 cell line were plated into a 96-well cell culture plate and treated with the polypeptides (1 to 3) for 24 hours. Then, the cells were treated with osimertinib (Tagrisso), an anticancer agent, which was subjected to a 1/10-fold serial dilution, for 24 hours and were confirmed using MTT. As an experiment to utilize the principle that NADH present in the mitochondria of a living cell reacts with MTT to form formazan, formazan was dissolved in DMSO and its absorbance was measured at 570 nm and thereby the growth activity of the cells was confirmed. The results are shown in FIGS. 11A and 11B.

Figure 11A:
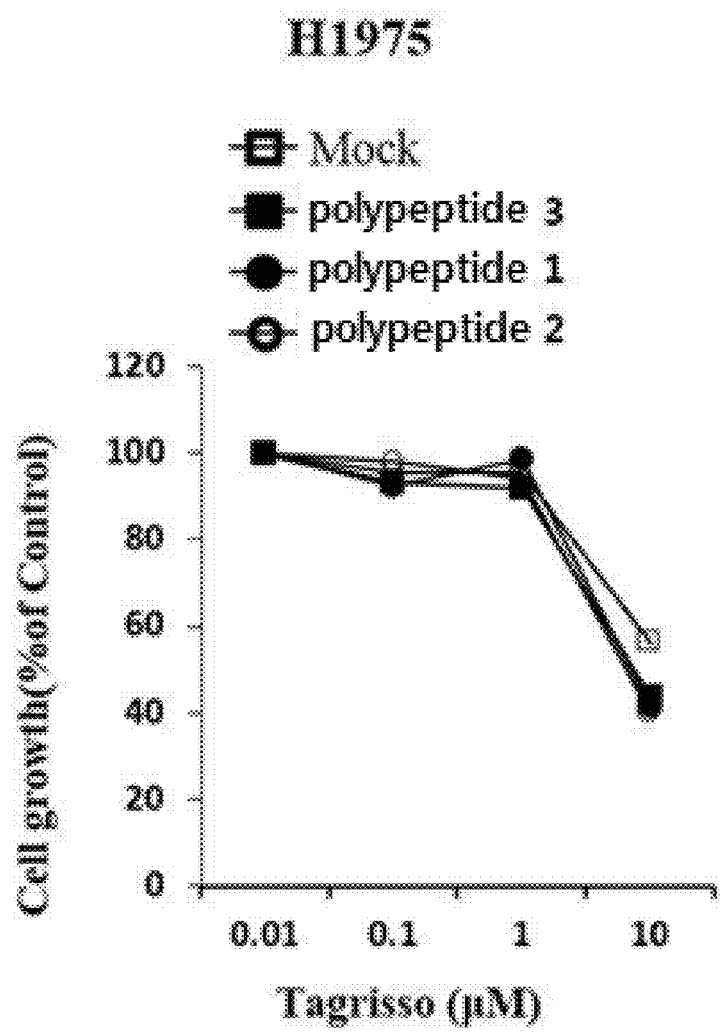
Figure 11B:
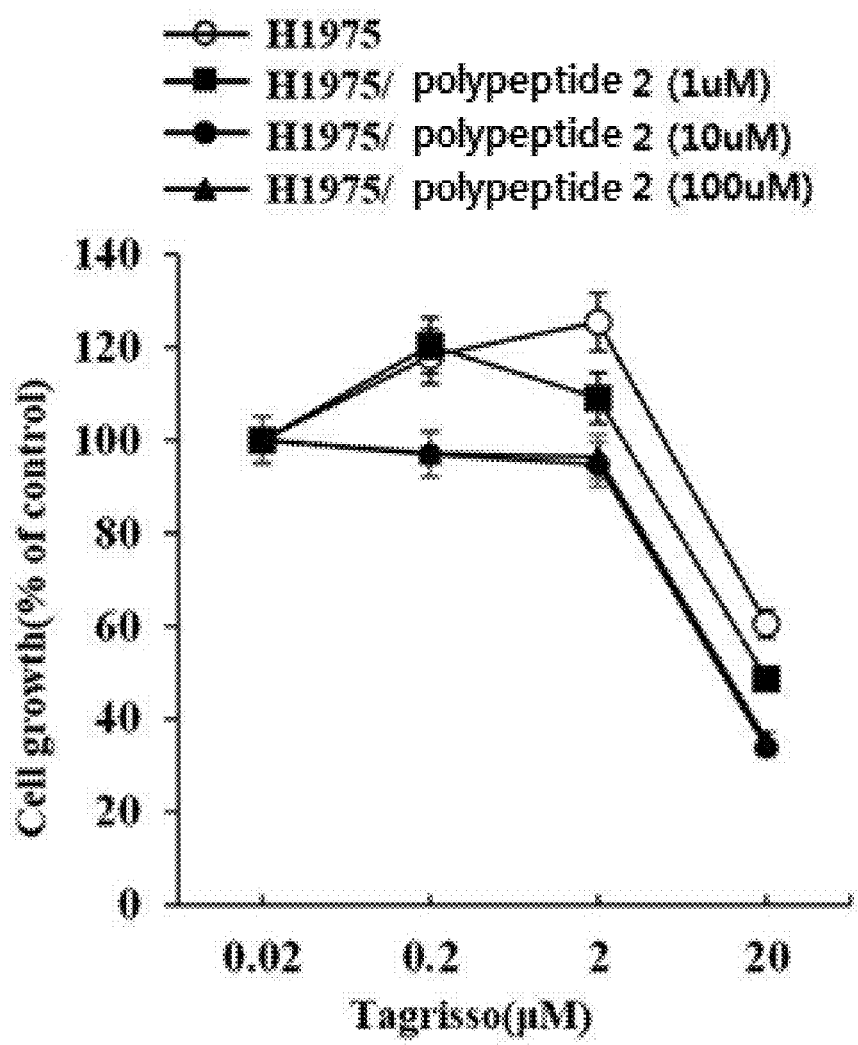

As a result, as can be seen in FIGS. 11A and 11B, it was confirmed that each of the polypeptides (1 to 3) reduced the resistance to osimertinib (Tagrisso), an anticancer agent.

These results show that the polypeptide 1, polypeptide 2, and polypeptide 3 have anticancer activity through the inhibition of autophagy.

Additionally, it was confirmed that when the cells were treated with polypeptide 2 at different concentrations, the resistance to osimertinib (Tagrisso), an anticancer agent, was reduced in a concentration-dependent manner.

Example 6: Confirmation of Effect of Anticancer Activity of Polypeptides

MCF7$^R$ cancer cell line having resistance to anticancer agents was constructed to have resistance by exposing to celastrol for a long period of time To examine the effects of the polypeptide 1 and the polypeptide 2 on the proteins of autophagy controlling mechanism, western blot was performed using each labeled antibody in the MCF7$^R$ cell line. The results are shown in FIG. 12.

Figure 12:
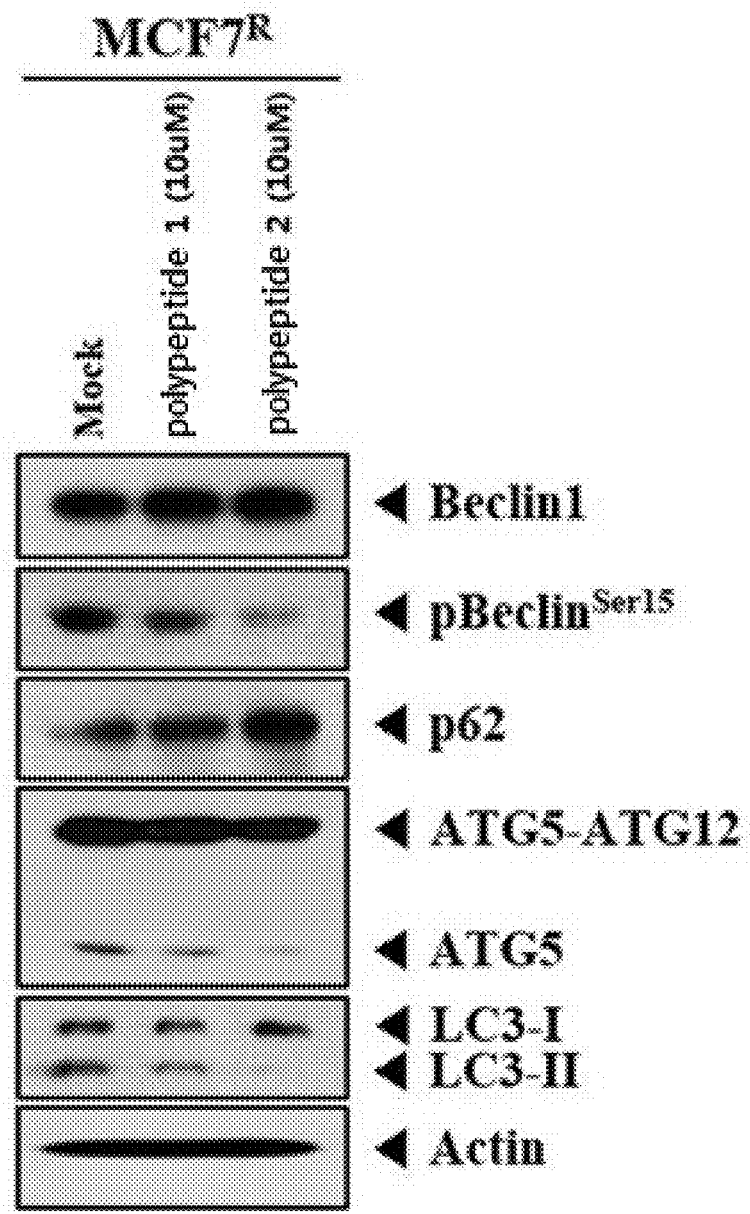
FIGS. 12 to 14C show the results according to Example 6 of the present invention.

As a result, as can be seen in FIG. 12, it was confirmed that when treated with the polypeptide 1 and the polypeptide 2, respectively, the expression level of p62 protein, which is an autophagy inhibiting molecule, was increased, whereas the expression levels of p-Beclin1, ATG5, ATG5-ATG12, LC3 I, and LC3 II proteins, which are autophagy activating molecules, were reduced.

Additionally, after the treatment with the polypeptide 2 in the MCF7$^R$ cell line, the immunofluorescence staining was performed.

Specifically, after treating the polypeptide 2 on the MCF7$^R$ cell line for 24 hours, the cells were fixed at room temperature using 4% formaldehyde. Then, the cells were reacted at room temperature for 30 minutes so as to prevent inaccurate binding to antibodies using PBS containing 0.1% BSA, and allowed to react with LC3 antibodies (cell signaling) at 4° C. for 24 hours. After removing the antibodies, the cells were washed with PBS and allowed to react with secondary antibodies (Thermo Fisher) labeled with Alexa 488 fluorescence at room temperature for 1.5 hours. After the reaction, the cells from which antibodies were removed were washed with PBS and stained with DAPI (Thermo Fisher) for 1 minute. The fluorescent staining was confirmed by confocal microscopy and the results are shown in FIG. 13.

Figure 13:
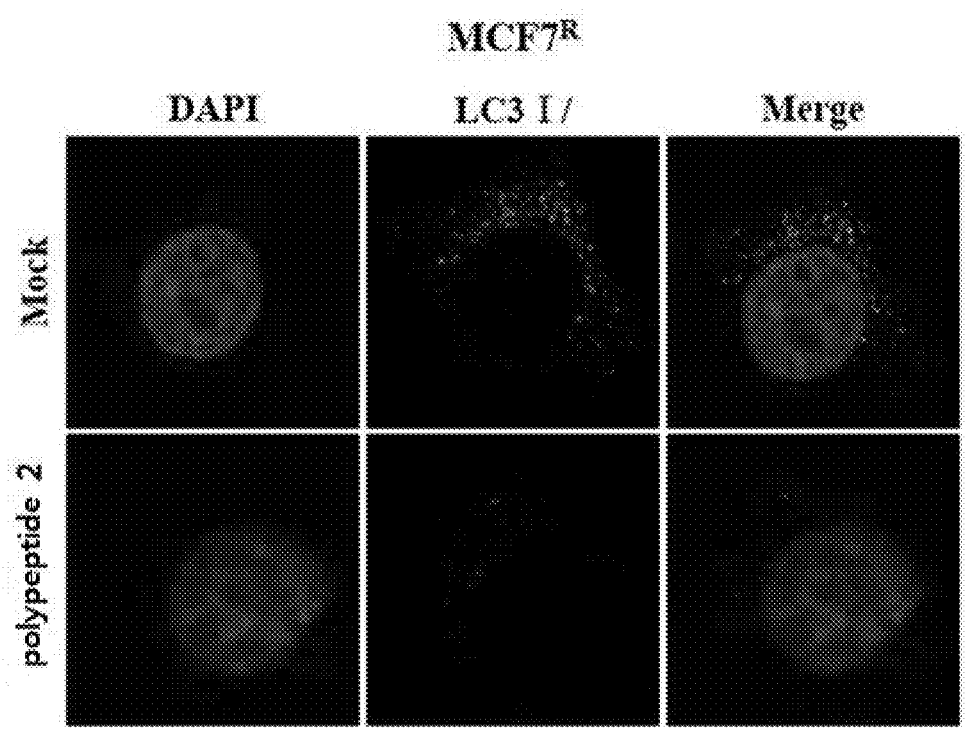

As a result, as can be seen in FIG. 13, it was confirmed that when the polypeptide 2 was treated on the MCF7$^R$ cell line, the expression level of LC3 puncta was lowered.

Additionally, after the treatment in the MCF7$^R$ cell line with the polypeptide 1, polypeptide 2, and polypeptide 3, respectively, the MTT assay was performed so as to confirm the resistance to anticancer agent.

Specifically, an equal number of cells of the H1975 cell line were plated into a 96-well cell culture plate and treated with the polypeptides (1 to 3) for 24 hours. Then, the cells were treated with an anticancer agent, which was subjected to a 1/10-fold serial dilution, for 24 hours and were confirmed using MTT. As an experiment to utilize the principle that NADH present in the mitochondria of a living cell reacts with MTT to form formazan, formazan was dissolved in DMSO and its absorbance was measured at 570 nm and thereby the growth activity of the cells was confirmed. The results are shown in FIGS. 14A, 14B and 14C.

Figure 14A:
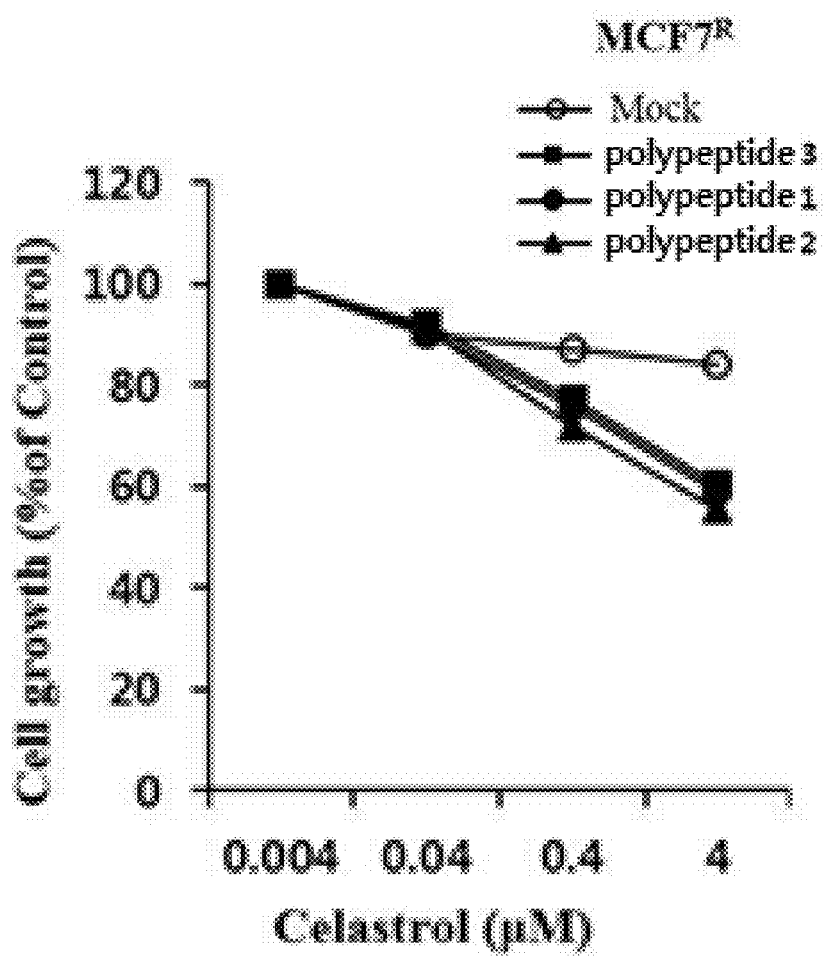
Figure 14B:
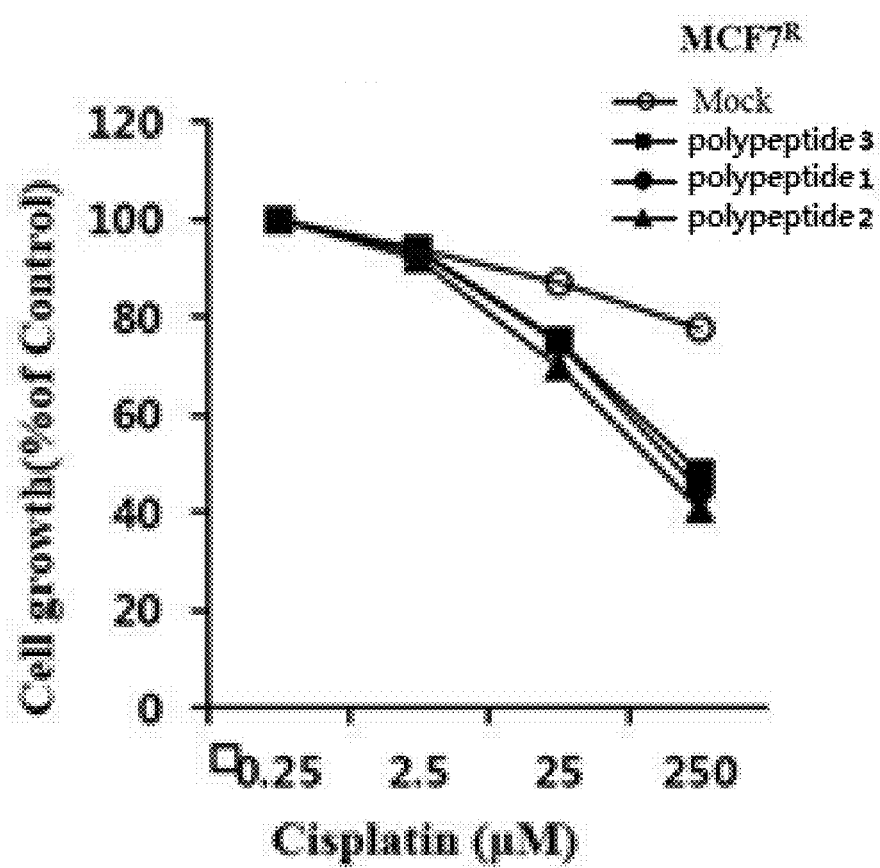
Figure 14C:
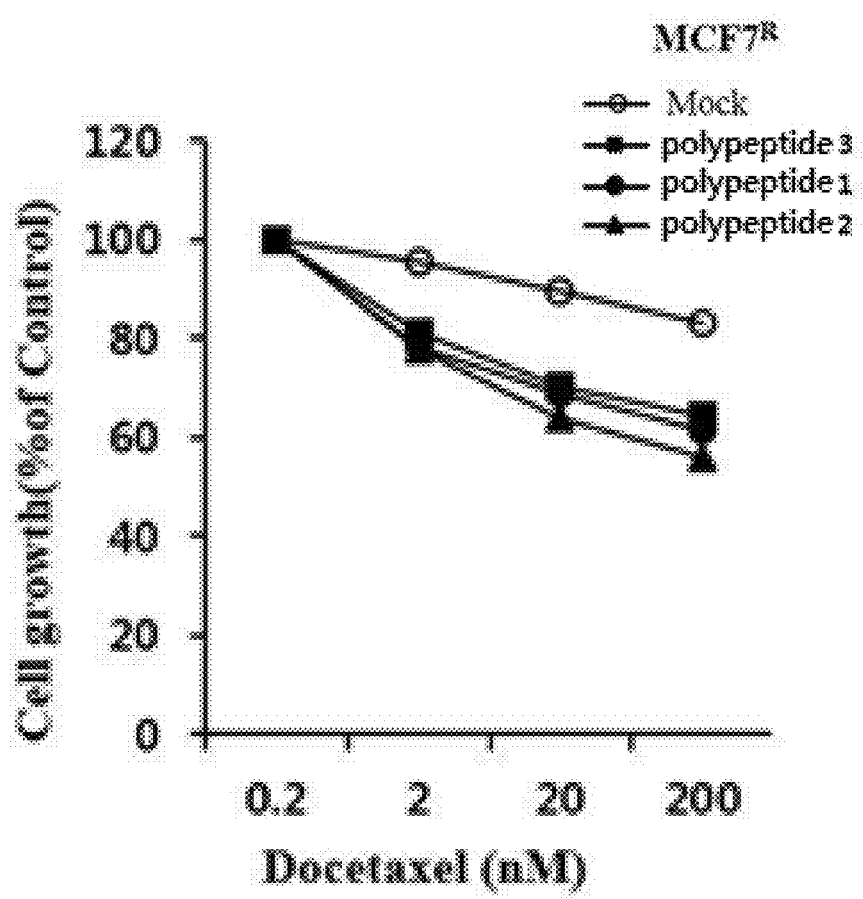

As a result, as can be seen in FIGS. 14A, 14B and 14C, it was confirmed that each of the polypeptides (1 to 3) reduced resistance to various anticancer agents, such as celastrol, cisplatin, docetaxel, etc., in the MCF7$^R$ cell line.

ADVANTAGEOUS EFFECTS OF THE INVENTION

As described above, the polypeptide according to the present invention has an effect of preventing or treating a neoplastic disease by inhibiting autophagy and it is also effective in inhibiting anticancer agent resistance.

What is claimed is:

1. A method of inhibiting autophagy in a cell, comprising administering to the cell a polypeptide consisting of the amino acid sequence of

X3-X1-T-X1-K—X2, wherein,
T is threonine,
K is lysine;
X1 is alanine, isoleucine, or proline;
X2 is alanine, or threonine; and
X3 is glutamine-threonine, glycine-asparagine-threonine, or serine.

2. The method of claim 1,
wherein X1 and X2 are alanine.

3. The method of claim 1,
wherein X1 is proline; and X2 is threonine.

4. The method of claim 1,
wherein X1 is isoleucine; and X2 is threonine.

5. The method of claim 1,
wherein X3 is glutamine-threonine.

6. The method of claim 1,
wherein X3 is serine.

7. The method of claim 1,
wherein X3 is glycine-asparagine-threonine.

8. The method of claim 1,
wherein the polypeptide inhibits autophagy in a cell by reducing the expression of at least one protein selected from the group consisting of p-AMPK, ATG5-ATG12, Beclin1, p-Beclin1, LC3-I, and LC3-II.

9. The method of claim 1,
wherein the polypeptide inhibits autophagy in a cell by increasing the expression of p-mTOR or p62 protein.

10. The method of claim 1,
wherein the polypeptide is labeled with any one labeling material selected from the group consisting of chromogenic enzymes, radioisotopes, chromophores, luminescent materials, fluorescers, magnetic resonance imaging (MRI) materials, super paramagnetic particles, and ultrasuper paramagnetic particles.

11. The method of claim 1,
wherein the cell is a tumor cell.

12. A method for treating a neoplastic disease comprising administering to a subject in need thereof a pharmaceutical compositing comprising a polypeptide consisting of the amino acid sequence of X3-X1-T-X1-K-X2,
wherein,
T is threonine,
K is lysine;
X1 is alanine, isoleucine, or proline
X2 is alanine, or threonine; and
X3 is glutamine-threonine, glycine-asparagine-threonine, or serine.

13. The method of claim 12,
wherein the neoplastic disease is selected from the group consisting of lung cancer, liver cancer, colon cancer, pancreatic cancer, stomach cancer, breast cancer, ovarian cancer, kidney cancer, thyroid cancer parathyroid cancer, esophageal cancer, prostate cancer, brain cancer, skin cancer, osteosarcoma, soft tissue sarcoma, glioma, lymphoma, nasopharyngeal cancer, larynx cancer, adrenal gland cancer, colon carcinoma, ureteral cancer, gallbladder cancer, bladder cancer, testis cancer, uterine cervical cancer, endometrial cancer, choriocarcinoma, head and neck cancer, malignant melanoma, leukemia, multiple myeloma, chronic myeloid leukemia, neuroblastoma, and aplastic anemia.

14. A method for inhibiting resistance to anticancer agents, comprising a polypeptide consisting of the amino acid sequence of X3-X1-T-X1-K—X2,
wherein
T is threonine,
K is lysine;
X1 is alanine, isoleucine, or proline
X2 is alanine, or threonine; and
X3 is glutamine-threonine, glycine-asparagine-threonine, or serine.

15. The method of claim 14,
wherein the composition has resistance to at least one anticancer agent selected from the group consisting of erlotinib, celastrol, cisplatin, docetaxel, osimertinib, taxol, pemetrexed, and tamoxifen.

* * * * *